United States Patent [19]

Conaway

[11] Patent Number: 4,688,387

[45] Date of Patent: Aug. 25, 1987

[54] METHOD FOR PRESERVATION AND STORAGE OF VIABLE BIOLOGICAL MATERIALS AT CRYOGENIC TEMPERATURES

[75] Inventor: Robert M. Conaway, Columbus, Ohio

[73] Assignee: Vital Force, Inc., Dublin, Ohio

[21] Appl. No.: 796,799

[22] Filed: Nov. 12, 1985

[51] Int. Cl.$^4$ .............................................. F24F 3/16
[52] U.S. Cl. ............................................ 62/78; 62/64; 435/1
[58] Field of Search ................ 62/64, 78; 435/1, 240, 435/241

[56] References Cited

U.S. PATENT DOCUMENTS

| 2,662,520 | 12/1953 | McMahon | 62/64 |
| 3,677,024 | 7/1972 | Segall | 62/64 |
| 4,423,600 | 1/1984 | McKenna | 62/78 |
| 4,462,215 | 7/1984 | Kuraoka et al. | 62/78 |
| 4,559,298 | 12/1985 | Fahy | 62/78 |

OTHER PUBLICATIONS

Mazur, Peter: Fundamental Cryobiology & Preservation of Organs by Freezing, Organ Preservation for Transplantation, Edit: A. M. Karow, Jr. & D. E. Pegg, Marcel Dekker, Inc., 2nd Edition, 1981, p. 144.

Fahey, G. M. et al.: "Prospects for Organ Preservation by Vitrification", Organ Preservation: Basic and Applied Aspects, Edit. D. E. Pegg, I. A. Jacobson, N. A. Halasz, MTP Press Limited, 1982, pp. 399–404.

Johnson, F. H. et al: "Kinetic Basis of Molecular Biology", John Wiley & Sons, Inc., 1954, pp. 286–368.

Primary Examiner—Ronald C. Capossela
Attorney, Agent, or Firm—George Wolken, Jr.

[57] ABSTRACT

A method for preserving biological material is disclosed in which the biological material is stored at cryogenic temperatures for long periods of time without incurring fatal damage to cells, tissues or organs. The process comprises freezing the biological material under conditions of temperature and pressure to avoid the formation of crystalline ice I at all times during the freezing process. Rather, metastable phases of ice are exploited to reduce damage to the biological material upon freezing, storage or subsequent thawing.

12 Claims, 1 Drawing Figure

METHOD FOR PRESERVATION AND STORAGE OF VIABLE BIOLOGICAL MATERIALS AT CRYOGENIC TEMPERATURES

BACKGROUND OF THE INVENTION

This invention relates to a method for the preservation of biological material and more particularly to a method for preserving viable biological material, typically cells, tissues or organs, at cryogenic temperatures for long periods of time, and in such a condition that a useful level of biological function is retained by said material and said biological function is capable of being re-established upon reintroduction into a host organism.

Many consider that the modern science of preservation of viable biological material with extreme cold ("cryobiology") began in 1950 with the discovery that human and bovine sperm, if properly treated, could withstand freezing to −80 deg. Celsius (approximately 193 deg. Kelvin). At these low temperatures, chemical activity within the biological material virtually ceases. Thus, normal process of metabolism, aging and death do not proceed, allowing the material to remain unchanged in the frozen state. This discovery had an immediate impact on agriculture in that it allowed the widespread use of artificial insemination with the semen of prize bulls. The procedures developed for sperm quickly led to the preservation by freezing of components of human blood (e.g. erythrocytes). Modern procedures make increasing use of frozen human blood cells.

During the 1960's, surgical procedures were developed for the successful transplantation of human kidneys and hearts. Transplants of human lungs, liver, and other organs have been developed in the intervening years, and new procedures are under investigation at many hospitals and universities. However, two major problems must be dealt with in organ transplantation; immunological rejection of the transplant by the recipient and the availability of a suitable donor organ. The problems are related in that an integral part of the problem of organ procurement is tissue typing to minimize the problems of immunological rejection by the host. Immunological considerations are implicit in the definition of what is or is not a "suitable" donor organ. Long-term storage of viable organs (i.e. for periods of months to years) will have a major impact on both problems. If long-term preservation of viable organs were technically feasible, organs could be procured when available and used when needed.

Present technology requires that an organ transplant be done within about 4–48 hours from the time the organ is removed from the donor. This severe time pressure creates several problems. Clearly, many patients who could have life-prolonging transplants are not able to locate a donor until the disease has so debilitated the patient that a transplant would no longer help. Also, the severe time constraints require that the donor and the recipient not be too widely separated geographically as the organ cannot stand much time in transit. This also severely limits the number of possible donors. Finally, the physicians' good-faith efforts to procure a viable organ in time to help a patient places severe psychological burdens on the donor's family at a time already very stressful for them.

Thus, if a technical means were available to preserve tissues and organs for long periods of time, suitable organs of a suitable type could be made available to the patient when needed. The creation of "tissue banks" or "organ banks" is recognized as a major problem in modern medicine, and is the area to which the present invention is directed.

We note that the present invention is primarily directed at the cryopreservation of tissues and organs. Blood can be stored for up to about three years in the frozen state and frozen human embryos have also been successfully introduced into a host mother. However, these techniques work well enough to be medically useful chiefly because the preserved material consists of separated single cells (in the case of blood) or an aggregate of a very small number of cells (typically 4 in the case of a frozen embryo). Thus, perfusion of cryoprotectant material (as discussed below) is much more easily accomplished and the removal of cryoprotectants is also much easier. Even here, however, there is a high mortality rate for the frozen biological material. Blood banks much prefer to store chilled, unfrozen blood for use within about three weeks. Frozen embryos likewise have a high mortality rate and typically several must be fertilized and frozen to insure a viable embryo will be available upon thawing. Thus, the present invention can advance the art of storage of single cells, and aggregates of small numbers of cells, by reducing the high mortality rate of the individual cells stored by freezing.

It has been firmly established that cells, tissues and organs can remain viable for months or years at cryogenic temperatures (i.e. temperatures below about 173 deg. Kelvin). "Low-temperature storage is no problem. Contrary to the usual impression, the challenge to cells during freezing is not their ability to endure the very low temperatures required for storage: it is the lethality of an intermediate zone of temperature ($\sim -15$ to $-50$ deg. Celsius) that a cell must traverse twice—once during cooling and once during warming." (quoted from Peter Mazur, "Fundamental Cryobiology and the Preservation of Organs by Freezing", P. 144 from *Organ Preservation for Transplantation*, ed. by A. M. Karow, Jr. and D. E. Pegg, 2nd Ed., 1981). Thus, long-term storage of cells, tissues and organs at cryogenic temperatures appears to be possible if the low temperatures can be obtained without incurring fatal damage to the biological material.

The are apparently two primary causes of fatal damage to cells during cooling. When cells are cooled fairly rapidly, crystals of ice tend to form within the cells. Water has the unfortunate property that, upon freezing, its volume increases by about 10%. Thus, the formation of ice within a cell causes substantial expansion of the cell membrane (and, frequently, expansion of intracellular organelles as well). Rupture often occurs and the cell loses its viability. It has become common knowledge in cryobiology that the formation of intracellular ice is almost always fatal to the cell.

The second primary cause of cell death on freezing is the loss of water from the interior of the cell by osmosis. If freezing is carried out slowly, ice will tend to form outside the cell rather than inside. With further cooling, water from the interior of the cell will pass by osmosis through the cell membrane to add to the growing extracellular ice crystals. In leaving the cell, large and often fatal concentrations of solutes remain behind in the interior of the cell. (Contraction by loss of water apparently does not affect the cell as much as expansion by freezing.) Thus, rapid cooling is usually fatal to the cell due to intracellular ice formation; slow cooling is usually fatal due to high concentrations of solute inside the cell.

The above discussion has described the salient features of the freezing of cells. The problems are analogous for freezing of tissues and organs, but complicated by several factors. Tissues usually have different types of cells with different membrane permeabilities, water content, ability to withstand expansion or contraction, etc. Heat and fluids may not rapidly transfer from one part of the tissue to another. Cells on the surface of the tissue or organ may be subjected to particularly severe conditions. It appears with the present state of knowledge that the basic biophysics of cell freezing determines to a large extent the lethality mechanisms encountered in the freezing of tissues or organs. Tissues and organs present additional serious technical complications, caused by the different properties of the different cells present, as well as heat and mass transfer problems within the tissue. But the major causes of cell death are apparently largely the same in cells, tissues and organs. The present invention addresses the problems in the basic biophysics of cell preservation by freezing. As pointed out below, the present invention is such that the additional complications introduced in preserving tissues, organs or, perhaps whole organisms, are minimized by the present invention.

The tremendous medical importance of tissue and organ preservation has generated tremendous research. Here we can only summarize a few salient features of the research most relevant to the background of the present invention. The fact that organ banks do not exist, and patients still die due to lack of donor organs, is strong evidence that the problem has not been solved and key components of the solution have yet to be discovered.

The objective of preservation of biological material in a viable state is to cause biological and chemical activity to cease without causing irreversible damage of fatal extent to the material in the process. Cooling the material to cryogenic temperatures would work if lethal cellular damage could be avoided during cooling, warming and during the storage of the material at low temperature. As noted above, the direct approach of simply cooling the material is not successful in preserving the viability of the samples, most likely due to the formation of intracellular or extracellular ice. Thus, prior work in the area has focused on attempting to avoid the formation of ice, or more likely, delay the onset of ice formation to as low a temperature as possible. To this end, a variety of materials known generically as "cryoprotectants" have been used. The cryoprotectants are typically glycerol, dimethylsulfoxide, ethylene glycol, propylene glycol, trimethylamine acetate, or other high molecular weight solutes capable of strongly hydrogen-bonding to water. The function of the cryoprotectant is to bond to cellular water to suppress the freezing point of the resultant solution as much as possible. Thus, the freezing point of water in the cellular system is effectively depressed, and lower temperatures can be achieved without causing cellular damage.

The use of cryoprotectants has several undesirable side effects. The higher the concentration of cryoprotectant, the more the freezing point is depressed. However, the higher the concentration of cryoprotectant, the more damage done to the cell by the cryoprotectant itself, and the harder it is to remove from multi-cellular materials such as tissues or organs. Thus, cryoprotectants are only effective in preserving single cells (such as sperm or blood) or biological material containing a very few cells (such as embryos). Even in these cases, concentrations of cryoprotectant that can be tolerated by the cells are not adequate to depress freezing as much as one would like. A large number of the cells preserved by freezing do not survive. (Unlike the case with tissues and organs, enough blood cells or embryos do survive to make freezing a medically useful procedure. But there is clear room for improvement.)

Large multi-cellular materials like tissues or organs have not been preserved for more than a few hours even with cryoprotectants. Research into better cryoprotectants and better ways to perfuse it through tissue or organs, and remove it therefrom, is a subject of active investigation at many institutions around the world.

A few investigators have examined the use of high pressures, usually in conjunction with cryoprotectant perfusion, in an attempt to achieve lower temperatures or lower the required concentration of cryoprotectants. H. O. McMahon (U.S. Pat. No. 2,662,520), P. E. Segall (U.S. Pat. No. 3,677 024), and G. M. Fahy and A. Hirsch (published in "Prospects for Organ Preservation by Vitrification", P. 399-404 of *Organ Preservation: Basic and Applied Aspects*, ed. D. E. Pegg, I. A. Jacobsen and N. A. Halasz, 1982) have considered the use of high pressure and cryoprotectants. The methods proposed by these investigators have not achieved wide use for reasons we believe are circumvented by the present invention.

Fahy and Hirsch demonstrate a 5% reduction in the amount of cryoprotectant needed to achieve a vitrification (presumably without the formation of ice crystals) by the application of 1000 atmospheres (atm) pressure. They speculate, but do not demonstrate that a 15% reduction could be achieved with application of 2000 atm pressure. Unfortunately, the cryoprotectant levels remaining in their experiments seriously affect the viability of the organs studied. Also, their work does not deal with the formidable problems of perfusing the cryoprotectant into and out of the organ in whatever concentration may be needed (at least 85% to 95% of levels used without high pressure). They also realize that a 5% reduction may appear to be very little for the application of such high pressure, but attempt to rationalize this by arguments that even a small reduction in cryoprotectant concentration can be crucial in determining toxicity (it most probably is for specialized cases). The net effect of these studies is that only a small reduction in cryoprotectant is achieved. Unanswered in their studies, but the subject of the present invention, is the conditions under which high pressure can radically reduce the necessary concentration of cryoprotectant, even to zero.

Segall's 1972 patent and McMahon's 1953 patent likewise attempt to use high pressures to avoid cellular damage on freezing. However, despite the fact that their concepts have been public knowledge for over 13 years and 32 years respectively, viable organ preservation is not a reality. In fact, their work receives virtually no mention by the more recent researchers in the field. We believe the reasons for this are clear.

A key factor in the invention disclosed by Segall is the stated necessity to purge the pressure chamber with inert gas, such as helium, and maintain the material in the presence of helium during pressurization. (Apparently, the invention of Segall requires helium to achieve uniform and relatively rapid heat transfer.) The results of our studies indicate that this is quite fatal to the preservation of viable biological material: the gas apparently infusing the cells under pressure, causing the cells to explode (rather like popcorn) upon return to normal pressures. The invention disclosed herein, contrary to the teaching of the prior art, specifically requires the exclusion of as much gas as possible.

The work by McMahon correctly points out that above about 2000 atm pressure, liquid water will not freeze to normal ice (so-called ice I) but, rather, will freeze to another phase of ice (ice III in modern terminology). It is also pointed out by McMahon that upon freezing to ice III, liquid water does not expand, as would be the case upon freezing to form ice I. Thus, one may hope that freezing under pressures sufficiently high to prevent the formation of ice I will not lead to significant cellular damage. The properties of water upon which this is based have been well known in the field for at least 50 years. However, the invention disclosed by McMahon requires that the biological material, once frozen under high pressure, be stored under equally high pressure for as long as may be required. This is apparently the major reason that McMahon's concepts have not found medical application, despite 32 years of public disclosure and 15 years in the public domain. The present invention, as disclosed herein, extends the concepts of McMahon in a way that permits the storage of the viable biological material at cryogenic temperatures (e.g. liquid nitrogen temperature) but at atmospheric pressure. Thus, the present invention requires only low temperature for the storage of organs, easily maintained by an organ bank. Unlike McMahon, the present invention requires high pressures only for organ bank "deposits" and "withdrawals", not a pressure vessel for every organ, maintained under high pressure for perhaps 35 years. "Recent work by Fahy (U.S. Pat. No. 4,559,298) combines the use of moderate pressures (not higher than 2000 atm) with perfusion of the sample by relatively high concentrations of cryoprotectants. The resulting material is subject to "vitrification" to a glassy state rather than freezing. The present invention, in contrast to the invention of Fahy, uses pressures much in excess of 2000 atm and markedly lower concentrations of cryoprotectants (even zero)."

Pressure propogates through matter at the speed of elastic deformation of the material (i.e. at the speed of sound in the material). Therefore, pressure changes are communicated to every part of the material very rapidly, and virtually instantaneously compared with changes in temperature. The present invention uses pressures to minimize cellular damage caused by freezing. Thus, the very difficult task of maintaining precise cooling rates throughout a large organ or tissue is avoided.

SUMMARY AND OBJECTS OF THE INVENTION

The present invention relates to a method for preservation of viable biological material using a combination of high pressure and low temperature in such a way as to substantially minimize damage to cells, organs and tissues on freezing or thawing.

A primary object of the present invention is to provide a method for preservation of biological cells, tissues or organs by freezing such that, upon subsequent thawing, substantial biological function is preserved.

A further object of the present invention is to utilize high pressure during freezing of biological material to substantially minimize damage to said biological material caused by freezing.

A further object of the present invention is to provide a method for storage of viable biological materials at cryogenic temperatures and atmospheric pressure.

A further object of the present invention is to provide a method for storage of viable biological material at cryogenic temperatures with a reduced amount of cryoprotectant being required to maintain viability.

A further object of the present invention is to provide a method for freezing biological materials while avoiding the formation of ice I.

Yet another object of the present invention is to provide a method of thawing cryogenic biological material without substantially damaging the biological function and viability of said material.

Another object of the present invention is to provide a method for storing biological material at cryogenic temperatures with the formation of metastable phases of ice.

A further object of the present invention is to provide a method for cryopreservation of tissues and organs which reduces the requirements for heat transfer within the tissue or organ.

DESCRIPTION OF PREFERRED EMBODIMENTS

Figure 1:
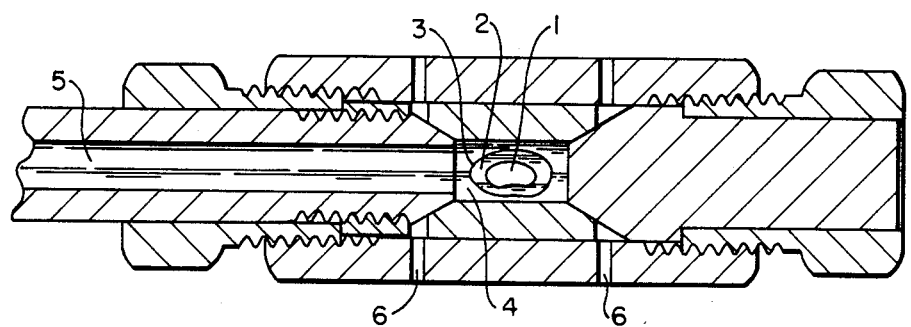
FIG. 1. A cross-sectional view of the pressure vessel containing the tissue sample, surrounding fluid, and protective enclosure.

FIG. 1 shows in cross-sectional view a typical pressure vessel containing a typical organ, 1, to be preserved by freezing to cryogenic temperatures. Although the present invention is equally applicable to tissues and small cellular aggregates, to be concrete we base our description on the preservation of a typical organ. Typically, the organ, 1, to be preserved is removed from the donor in a viable state. It is then typically perfused with a suitable solution, typically saline, saline with cryoprotectants, or another suitable solution. The solution perfusing the organ is denoted, 2, in FIG. 1. The organ is typically then tightly sealed in a suitable container, typically a flexible plastic, 3 in FIG. 1. Care must be taken that no extraneous gases are entrapped in the container, 3 along with the organ to be preserved, 1, as such entrapped gases tend to be forced into the cellular structure under high pressures. The container, 3, must be capable of transmitting applied hydrostatic pressure to the organ, 1. Therefore, the container, 3 should either be suitably flexible to contract under pressure, thereby equalizing the internal pressure with the external pressure, or have an alternative means for equalizing the pressure applied externally to the container with that inside said container.

While in transit from the location of the donor to the preservation apparatus, container, 3, along with organ, 1, and solution, 2, are typically packed in ice to retard degradation of the biological viability of the organ. Nevertheless, time should be considered of the essence in transporting the organ from the donor to the preservation apparatus.

The container, 3, along with its contents is then typically placed into the cavity of the pressure vessel, 4. To facilitate application of hydrostatic pressures, the cavity, 4, is typically filled with a fluid, and hydrostatic pressure applied by means of opening, 5. A typical pressure vessel will also contain pressure relief openings, 6. For the present application, the pressure vessel must be able to withstand cryogenic temperatures as well as high pressures.

The pressure vessel in then typically placed into an apparatus (not shown) in which controlled pressures can be applied and controlled cooling can simultaneously be applied to the samples, as is standard in the art.

The currently preferred embodiment of the present invention involves maintaining the sample, 1, at approximately the ambient temperature at which it was placed into the container, while the applied pressure is steadily increased. As noted above, the formation of ice I leads to an expansion of the water in the cells upon freezing to ice I. This is known to be very harmful to biological material. Thus, the applied pressure is typically increased a value where ice I will no longer form on cooling, typically above about 2,100 atmospheres (atm). At pressures from about 2,108 atm to 3,506 atm water will freeze to the ice III phase on cooling. From 3,506 atm to 6,343 atm water will freeze to the ice V phase on cooling, while above 6,343 atm ice VI will form (at least up to about 19,000 atm). However, all of these ice phases except ice I contract upon freezing, thus avoiding the presumed major mechanism of cellular damage.

An alternative embodiment of the present invention is to increase the pressure on the organ, 1, without cooling, until solidification occurs. It is well known from the phase diagram of water that the freezing point of water decreases with pressure to a minimum freezing point of about $-20$ deg. Celsius at an applied pressure of about 2,100 atm. At still higher pressures, the freezing point of water continuously increases again, reaching values in excess of $+50$ deg. Celsius for pressures of about 13,600 atm. (Thus, at these high pressures, melting ice is quite hot.) If the organ, 1, is initially placed into the pressure apparatus at a temperature of typically in the neighborhood of 0 deg. Celsius, applied pressures of about 6,000 atm will be sufficient to cause solidification without additional cooling. Either ice V or ice VI will form depending on the precise conditions, since 0 deg. Celsius is very close to the phase boundary between these two phases (the transition occurring at 0.16 deg. Celsius and 6,174 atm in pure water).

Using either of the above methods, the sample under high pressure is now cooled to cryogenic temperatures, typically by immersion of the entire pressure vessel in liquid nitrogen or an equivalent cryogenic fluid. Temperatures below $-150$ deg. Celsius are typically attained. At these temperatures, all biological activity has stopped and the chemistry of the cells has likewise ceased, allowing storage for at least several years.

Storage of a biological material at low temperatures and under high pressure is not as convenient as storage under low temperature alone. Thus, the pressure must be relieved without leading to the formation of ice I. Typically, the present invention uses rapid release of applied pressure to quench the high pressure phase of ice already formed. Based upon phase diagrams of water, it is thought that the trapped metastable phase of water formed is the metastable phase of ice known as ice Ic. However, other evidence from the physical chemistry of water indicates that other phases of ice (II, VI and IX) are formed at high pressure and low temperature. These phases seem to be themselves metastable in that, upon return to atmospheric pressure, they persist for an indefinite period. (This phenomena seem to be the basis for producing many of these phases of ice for structural studies in the first place.) Thus, the precise phase of ice formed by the present process is not precisely determined. But the relative lack of damage to the biological material is strong indication that it is probably not ice I.

The detailed structure of the solid phase produced by the process of the present invention needs much more investigation. In all events, however, the process of preservation by freezing under pressure disclosed here permits the formation of a metastable phase of ice which lacks the harmful effects of ice I on the cells.

The process disclosed here is not troubled by the problems of achieving a uniform cooling at all cells throughout a bulk tissue or organ. Since the present process is based upon the propagation of pressure waves through the material (at the speed of sound in the material), pressure uniformity is easily achieved. The pressures used permit enough margin of safety that precise temperature control throughout the sample is not as crucial as in previous methods of preservation.

For thawing the material after storage, the process is reversed. Typically, the material is reintroduced into the pressure apparatus and placed under applied hydrostatic pressures in excess of 2,100 atm. The temperature of the material is then raised, typically in a uniform manner by microwave or radiofrequency heating. The pressure is then relieved to recover the viable organ.

I claim:

1. A method of preserving and storing biological material comprising the steps of:
    (a) removing biological material from a donor organism and placing said material into a container capable of withstanding high pressures as applied in step (c) and capable of withstanding cryogenic temperatures as applied in step (d); and
    (b) introducing a substantially biologically inert liquid into said container in contact with said material in such manner as to substantially displace and expel from said container substantially all gases; and
    (c) pressurizing said container and said liquid to a pressure sufficient to prevent the formation of ice I upon subsequent cooling; and
    (d) cooling said container and its contents to a cryogenic temperature below approximately 173 deg. Kelvin; and
    (e) depressurizing said container and contents to normal atmospheric pressure while maintaining said cryogenic temperature, said depressurizing performed in such manner as to maintain in metastable state a phase other than crystalline ice I.

2. A method as in claim 1, further comprising the step, performed immediately following step (a) of claim 1, of:
    Perfusing said material with a solution containing at least one cryoprotective agent.

3. A method as in claim 2, wherein said pressurizing step (c) is to pressures sufficiently high to avoid the formation of ice III upon subsequent cooling, in excess of approximately 3,500 atmospheres.

4. A viable biological material preserved at cryogenic temperatures produced in accordance with the method of claim 3.

5. A method as in claim 3 wherein said pressurizing step (c) is performed sufficiently rapidly to avoid substantial damage to said biological material.

6. A method as in claim 2, wherein said pressurizing step (c) is to pressures sufficiently high to cause the substantial cessation of biological activity by vitrification of said cryoprotectant-perfused biological material.

7. A method as in claim 6 wherein said pressurizing step (c) is performed sufficiently rapidly to avoid substantial damage to said cryoprotectant-perfused biological material.

8. A method as in claim 2, wherein said pressurizing step (c) is to pressures sufficiently high to cause the substantial cessation of biological activity by vitrification of said cryoprotectant-perfused biological material.

9. A method of restoring the viability of a biological material stored in accordance with claim 2 comprising the steps of:
  (a) repressurizing said container and said liquid to a pressure sufficient to avoid the formation of crystalline ice I upon subsequent warming; and
  (b) raising the temperature of said container and contents to a temperature of at least 273 deg. Kelvin; and
  (c) depressurizing said container and contents to atmospheric pressure; and
  (d) flushing said cryoprotective agents out of said biological material.

10. A method as in claim 1 or claim 2 wherein said cryogenic temperature of step (d) is below approximately 123 deg. Kelvin obtained by means of immersion in a cryogenic liquid substantially similar to liquid nitrogen.

11. A method of restoring the viability of a biological material stored in accordance with claim 1 comprising the steps of:
  (a) repressurizing said container and said contents to a pressure sufficiently high to avoid the formation of crystalline ice I upon subsequent warming; and
  (b) raising the temperature of said container and contents to a temperature of at least 273 deg. Kelvin; and
  (c) depressurizing said container and contents to atmospheric pressure.

12. A viable biological material preserved at cryogenic temperatures produced in accordance with the method of claim 1.

* * * * *